(12) United States Patent
Hoste et al.

(10) Patent No.: US 6,562,022 B2
(45) Date of Patent: May 13, 2003

(54) CATHETER WITH ENHANCED REINFORCEMENT

(75) Inventors: John H. Hoste, Fallbrook, CA (US); Howard Graham, Temecula, CA (US); David K. Wrolstad, Temecula, CA (US); Bruce Wilson, Escondido, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 51 days.

(21) Appl. No.: 09/736,856

(22) Filed: Dec. 13, 2000

(65) Prior Publication Data

US 2002/0072729 A1 Jun. 13, 2002

(51) Int. Cl.[7] ............................................. A61M 25/00
(52) U.S. Cl. ..................... 604/524; 604/264; 138/123
(58) Field of Search .......................... 604/524, 282, 604/280, 526, 527, 48, 93.01, 264, 523, 533, 534, 537, 525; 138/125, 130, 132, 127, 153, 172, 123, 124

(56) References Cited

U.S. PATENT DOCUMENTS

| | | | | |
|---|---|---|---|---|
| 3,485,234 A | * | 12/1969 | Stevens | 128/2 |
| 3,924,632 A | * | 12/1975 | Cook | 128/348 |
| 4,200,126 A | * | 4/1980 | Fish | 138/143 |
| 4,425,919 A | * | 1/1984 | Alston, Jr. et al. | 128/658 |
| 4,516,972 A | * | 5/1985 | Samson | 604/282 |
| 4,586,923 A | * | 5/1986 | Gould et al. | 604/95 |
| 4,817,613 A | * | 4/1989 | Jaraczewski et al. | 128/658 |
| 5,037,404 A | | 8/1991 | Gold et al. | 604/282 |
| 5,667,499 A | * | 9/1997 | Welch et al. | 604/282 |
| 5,741,325 A | | 4/1998 | Chaikof et al. | |
| 5,741,429 A | * | 4/1998 | Donadio, III et al. | 216/8 |
| 5,824,040 A | * | 10/1998 | Cox et al. | 623/1 |
| 5,891,114 A | * | 4/1999 | Chien et al. | 604/282 |
| 5,927,345 A | * | 7/1999 | Samson | 138/127 |
| 5,947,940 A | * | 9/1999 | Beisel | 604/282 |
| 6,027,529 A | * | 2/2000 | Roychowdhury et al. | 623/1 |
| 6,143,013 A | | 11/2000 | Samson et al. | 606/192 |
| 6,159,220 A | | 12/2000 | Gobron et al. | 606/127 |
| 6,258,195 B1 | * | 7/2001 | Holman et al. | 156/166 |
| 6,290,692 B1 | * | 9/2001 | Klima et al. | 604/524 |

* cited by examiner

*Primary Examiner*—Charles G. Freay
*Assistant Examiner*—Han L. Liu
(74) *Attorney, Agent, or Firm*—Fulwider Patton Lee & Utecht, LLP

(57) ABSTRACT

An intracorporeal catheter such as a guiding catheter employed for intravascular procedures which generally has an elongated catheter shaft with a polymeric wall with a multistrand reinforcing structure wherein the strands at a plurality of cross point locations of the reinforcing structure are secured together to hold at least part of the braided reinforcing structure in a desired shape for utilization. The strands may be metallic or polymeric or mixtures thereof. The strands can be secured together at the cross points thereof by a variety of ways. In one embodiment a plurality of the strands forming the reinforcing structure are formed of metal and are provided with a coating of solder so that the strands can be secured together by applying heat to the strands at the cross point locations to melt the solder and allow a solidified solder connection between the strands to be formed upon cooling while holding at least the portion of the reinforcing structure having secured cross points while holding the portion of the reinforcing structure in the desire shape. Other embodiment involve other methods of securing the strands at the cross points including welding, brazing, adhesives or mechanical connections.

33 Claims, 2 Drawing Sheets

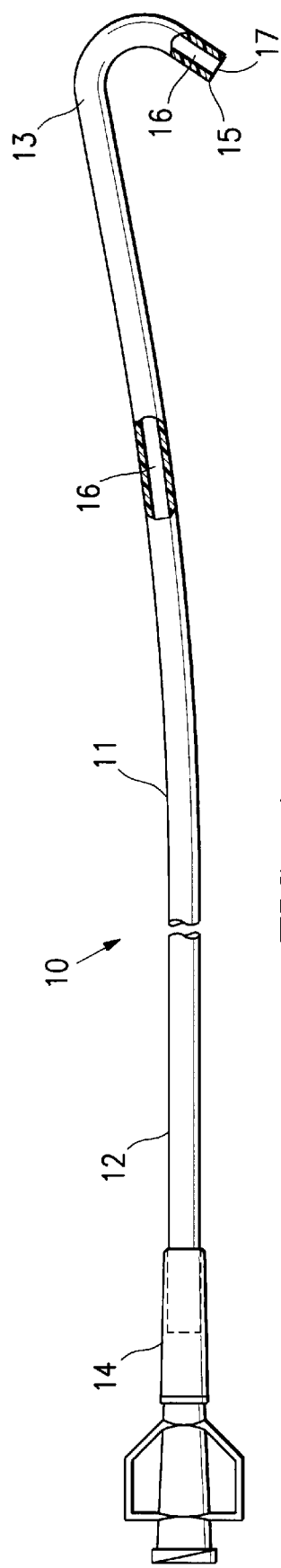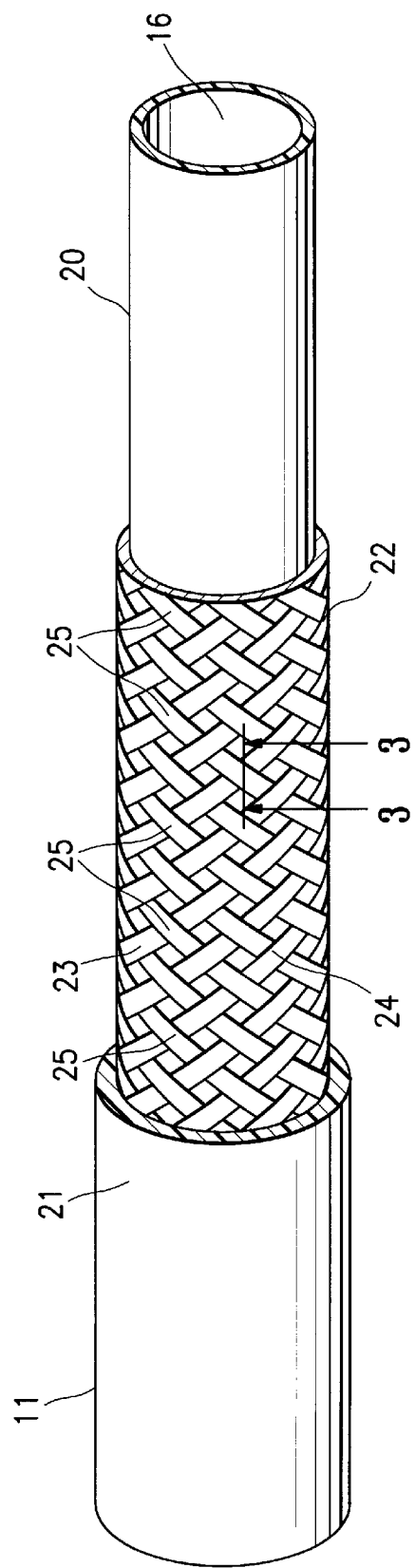
FIG. 1
FIG. 2

CATHETER WITH ENHANCED REINFORCEMENT

FIELD OF INVENTION

The invention relates to the field of intraluminal catheters, and particularly to guiding catheters suitable for intravascular procedures such as angioplasty, stent deployment and the like.

BACKGROUND OF THE INVENTION

In percutaneous transluminal coronary angioplasty (PTCA) procedures a guiding catheter having a shaped distal section is percutaneously introduced into the patient's vasculature by a conventional "Seldinger" technique and then advanced through the patient's vasculature until the shaped distal section of the guiding catheter is adjacent to the ostium of a desired coronary artery. The proximal end of the guiding catheter, which extends out of the patient, is torqued to rotate the shaped distal section and, as the distal section rotates, it is guided into desired coronary ostium. The distal section of the guiding catheter is shaped so as to engage a surface of the ascending aorta and thereby seat the distal end of the guiding catheter in the desired coronary ostium and to hold the catheter in that position during the procedures when other intravascular devices such a guidewires and balloon catheters are being advanced through the inner lumen of the guiding catheter.

In the typical PTCA or stent delivery procedures, the balloon catheter with a guidewire disposed within an inner lumen of the balloon catheter is advanced within the inner lumen of the guiding catheter which has been appropriately positioned with its distal tip seated within the desired coronary ostium. The guidewire is first advanced out of the distal end of the guiding catheter into the patient's coronary artery until the distal end of the guidewire crosses a lesion to be dilated or an arterial location where a stent is to be deployed. A balloon catheter is advanced into the patient's coronary anatomy over the previously introduced guidewire until the balloon on the distal portion of the balloon catheter is properly positioned across the lesion. Once properly positioned, the balloon is inflated with inflation fluid one or more times to a predetermined size so that in the case of the PTCA procedure, the stenosis is compressed against the arterial wall and the wall expanded to open up the vascular passageway. In the case of stent deployment, the balloon is inflated to plastically expand the stent within the stenotic region where it remains in the expanded condition. Generally, the inflated diameter of the balloon is approximately the same diameter as the native diameter of the body lumen being dilated so as to complete the dilatation or stent deployment but not overexpand the artery wall. After the balloon is finally deflated, blood flow resumes through the dilated artery and the dilatation catheter and the guidewire can be removed therefrom.

Generally, the stent deployment occurs after a PTCA procedure has been performed at the stenotic site. However, recently, in some situations the stent deployment and lesion dilatation is accomplished simultaneously.

In addition to their use in PTCA and stent delivery procedures, guiding catheters are used to advance a variety of electrophysiology catheters and other therapeutic and diagnostic devices into the coronary arteries, the coronary sinus, the heart chambers, neurological and other intracorporeal locations for sensing, pacing, ablation and other procedures. For example, one particularly attractive procedure for treating patients with congestive heart failure (CHF) involves introduction of a pacing lead into the patient's coronary sinus and advancing the lead until the distal end thereof is disposed within the patient's great coronary vein which continues from the end of the coronary sinus. A second pacing lead is disposed within the patient's right ventricle and both the left and right ventricle are paced by the pacing leads, resulting in greater pumping efficiencies and greater blood flow out of the heart which minimizes the effects of CHF.

Current construction of many commercially available guiding catheters include an elongated shaft of a polymeric tubular member with reinforcing strands (usually metallic or high strength polymers) within the wall of the tubular member. The strands are usually braided into a reinforcing structure. The strands are for the most part unrestrained except by the braided construction and the polymeric matrix of the catheter wall. The desired shape in the distal section of the catheter, which facilitates its deployment at the desired intracorporeal location such as the coronary sinus, is typically formed by holding the distal section in the desired shape and heat setting the polymeric material in the distal section of the catheter wall to maintain the desired shape. There is usually some spring-back after the heat formation due to the reinforcing braid, but this is usually compensated for in the shape the catheter is held in during the heat setting.

Clinical requirements for utilizing guiding catheters to advance electrophysiology catheters and the like have resulted in an increase in the transverse dimensions of the inner lumens of guiding catheters to accommodate a greater variety of larger intracorporeal devices and a decrease in the outer transverse dimensions of the guiding catheter to present a lower profile and thereby facilitate further advancement within the patient's body lumens and openings. These catheter design changes have required a reduction in the ratio of polymer to stranded reinforcement in the catheter wall which results in manufacturing problems with respect to the shaping of the distal end of the catheter. With such thin polymeric walls, the polymer mass of the catheter wall can be insufficient to control the reinforcing braid within the wall to the desired shape.

What has been needed is a catheter design which would allow for continued thinning of the catheter wall while facilitating the formation of the shape of the distal end of the catheter. The present invention satisfies these and other needs.

SUMMARY OF THE INVENTION

The invention is generally directed to a catheter system with an improved multistrand reinforcing structure which adds to the strength of the catheter wall while holding the shape of the distal end of the catheter to closer tolerances.

The guiding catheter of the invention has an elongated shaft with a preshaped distal shaft section to facilitate placement of the distal tip of the catheter. The shaft has a multistrand reinforcement, preferably within the wall of the shaft, which is formed into the desired shape of the catheter. While the distal shaft section of the catheter is held in the desired shape, such as by a mandrel, at a plurality locations where individual strands of the multistrand reinforcement cross, hereinafter called cross points, the crossed strands are bonded or otherwise secured together so as to retain the reinforcing structure, and therefore the distal shaft section of the catheter, in desired shape. The multistrand reinforcing structure may be formed by braiding, winding or the like a plurality of strands so as to have a plurality of cross points.

The cross points of the stranded reinforcement can be bonded or secured together in a variety of methods, such as by soldering, welding (e.g. laser welding), brazing, adhesives, mechanical connections and the like. Materials other than the strand material may be used to bond or otherwise secure the strands.

The elongated catheter shaft may have varied properties along the length. Typically, the elongated catheter shaft has increased flexibility in the distal direction by forming the catheter wall with polymeric materials having decreasing stiffness, i.e. distally decreasing durometers.

One embodiment of forming the catheter shaft includes extruding a polymeric tube which forms the inner lining for the catheter shaft and braiding multiple strands (e.g. 12, 16 or 24 strands) of suitable material, e.g. stainless steel, in the form of wire or ribbon about the inner tubular member. At least one of the strands, and preferably about one half or more of the strands, has a thin coating of solder on the surface thereof. In this manner, when the partially completed product of the braided reinforcing structure on the inner tubular member is held in the desired shape, the location where the strands cross, i.e. the cross points, are heated to melt the solder on the surface of at least one of the strands, and then cooled to solidify the solder and bond the strands at the cross points while being held in the desired shape. The reinforcing structure formed by the strands is thus fixed in the desired shape for the catheter. An outer polymer jacket may then be provided on the exterior of the reinforcing structure by heat shrinking a polymeric tube onto the surface of the reinforcing braid. If the temperature of the heat shrinking and solder melting are made compatible, the strands may be soldered simultaneously while the outer polymer layer is shrunk fit onto the reinforcing braid.

The braided reinforcing structure extends through most of the length of the elongated catheter shaft except for the distal tip which is usually provided with relatively flexible non-reinforced polymeric tubular member to provide non-traumatic characteristics to the distal tip. However, strands usually need to be secured together in cross points of the shaped portion of the catheter such as the distal shaft section.

In another embodiment, the inner layer and the braided structure are formed in essentially the same manner as described above for the first embodiment, except that crossed strands are bonded together by welding at a plurality of strand cross points along a substantial length of the shaft. Preferably, the cross points locations which are welded or otherwise bonded are equally disposed circumferentially about the braided reinforced structure and longitudinally along its length to provide rigidity to the braided structure. Laser welding (e.g. welding with a YAG-type laser) of the cross strands or other suitable welding methods may be employed depending upon the nature and composition of the strand.

In another embodiment, an adhesive such as cyanoacrylate is applied to the crossed strands at the cross points. In yet another embodiment, the strands at the cross points are brazed to obtain the same effects. In another similar embodiment, mechanical connections of a variety of sorts such as clips, staples, wires and the like are employed to secure or bond the strands of the cross points together and thereby fix the braided structure in the desired shape.

After the braided reinforcing structure is fixed into the desired shape by securing the crossed strands at a plurality of cross points in a desired pattern, a polymeric matrix is applied by suitable methods such as shrink fitting and the like to the exterior of the braided reinforcing structure.

Fixing the shape of the braided reinforcing structure by bonding or otherwise securing the crossed strands of the braided reinforcement strengthens the braided structure and minimizes the support the polymeric material must add to the catheter shaft structure. This allows for much thinner polymer layers, resulting in thinner catheter walls and provides for more supportive and consistent catheter shapes.

These and other advantages of the invention will become more apparent from the following detailed description of the invention and the accompanying exemplary drawings.

BRIEF DESCRIPTION OF THE DRAWINGS

FIG. 1 is a schematic, elevational view of a guiding catheter embodying features of the invention.

FIG. 2 is a cutaway perspective view of the elongated shaft of the catheter shown in FIG. 1.

DETAILED DESCRIPTION OF THE INVENTION

Figure 3:
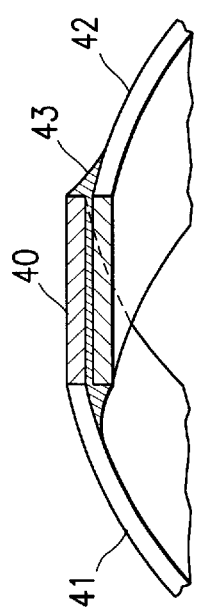
FIG. 3 is a cross-section of a cross point in which the strands are bonded by welding.

FIG. 1 illustrates a catheter 10 embodying features of the invention which generally includes an elongated catheter shaft 11 with a proximal shaft section 12 and a shaped distal shaft section 13, an adapter 14 mounted on the proximal end of proximal shaft section 12, a non-traumatic distal tip 15 and an inner lumen 16 which extends within the catheter shaft 11 from the proximal end thereof to a port 17 located in the distal end of the shaft.

As shown in greater detail in FIG. 2, the elongated catheter shaft 11 is formed of inner polymeric layer 20, an outer polymeric layer 21 and a braided reinforcing structure 22 formed of multiple strands 23 disposed between the inner and outer polymeric layers. At multiple cross point locations 24 where two strands cross over, the strands are bonded or secured together by welding with the weldment being designated by reference number 25. The strands at every cross point need not be secured; however, the more cross points that are secured, the stiffer the reinforcing structure will be. Secured cross points may be provided in a pattern, as shown in FIG. 2 being every other cross point in a longitudinal line, or they may be in a random pattern. A wide variety of patterns may be utilized.

FIG. 3 illustrates a transverse cross-section through a secured cross point 24 shown by the lines 3—3 in FIG. 2. The upper strand is designated by the reference number 26 and the lower strand by reference number 27. The weldment 25 secures the two strands together.

Figure 4:
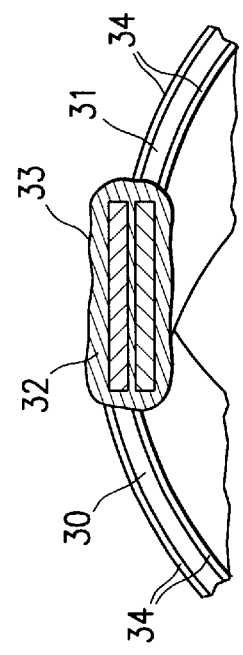
FIG. 4 is a cross-section of a cross point in which the strands are bonded by solder.

In FIG. 4 the upper strand 30 and the lower strand 31 of the cross point 32 are secured together by soldered joint 33. In this embodiment one or more of the strands which form the reinforcing structure have a solder coating 34. A hot tip probe may be applied to each cross point 32 in which a bond is desired to melt the solder coating 34 on the ribbon or wire to form the soldered joint 33 between the strands 30 and 31. Alternatively, the entire stranded reinforced structure can be heated to the temperature at which the solder melts and then cooled to form a soldered joint at each cross point. For stainless steel strands suitable solders include pure tin and tin-silver solders. The solder coating on the surface of the strands to be braided should be at least about 500 micro-inches thick. Generally, the coating thickness of solder on the strands should not exceed about 1500 micro-inches and preferably not less than about 50 micro-inches.

Figure 5:
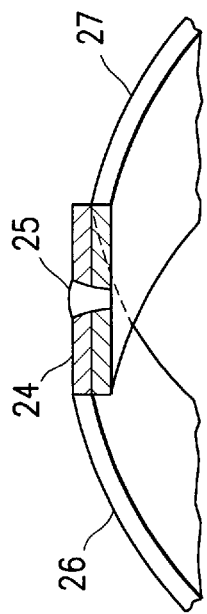
FIG. 5 is a cross-section of a cross point in which the strands are bonded by adhesive.

FIG. 5 illustrates a cross point 40 of upper strand 41 and lower strand 42 which are secured together by means of an adhesive 43.

Figure 6A:
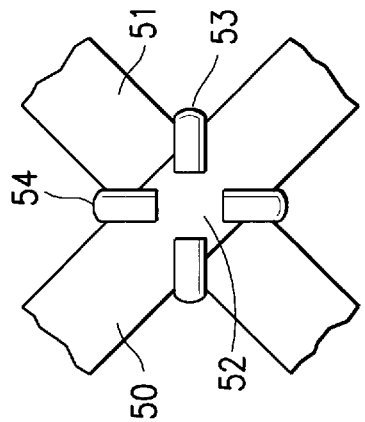
FIG. 6A is a top view of a cross point in which the strands are mechanically secured by clips.
Figure 6B:
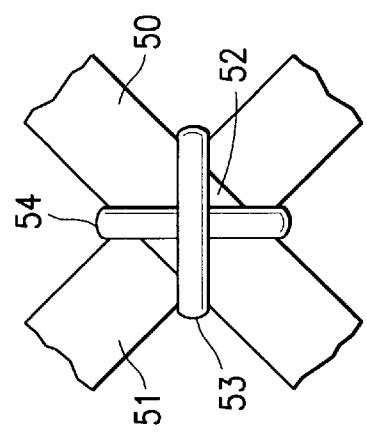
FIG. 6B is a bottom view of a cross point shown in FIG. 6A.

In FIGS. 6A and 6B upper strand 50 and lower strand 51 are secured together at their cross point 52 by two U-shaped clips 53 and 54. As recognized by those skilled in the art, a wide variety of other mechanical connecting elements may be employed to secure the strands at their cross points. The clips 53 and 54 may be made of suitable material such as 304 stainless steel.

Guiding catheters designed for coronary artery access generally have a length from about 90 to about 110 cm, preferably about 100 cm. The wall thickness of the catheter shaft ranges from about 0.004 to about 0.01 inch. The outer polymeric layer is about 0.001 to about 0.006. The inner polymeric layer is about 0.001 to about 0.002 inch. The presently preferred polymeric materials are various durometers of PEBAX or nylon. Other suitable polymeric materials include polyimide and polyurethanes. A variety of thermoplastic and thermoelastic polymers, copolymers and blends may be employed.

The strands which are braided or wound to form the reinforcing structure may have a round (wire) or rectangular (ribbon) and their dimensions depends upon their mechanical properties and the stiffness required for the reinforcing structure. For stainless steel wire a diameter of about 0.001 to about 0.003 inch is suitable. For stainless steel ribbon, the transverse cross sectional dimensions are about 0.0005 to 0.002 by about 0.003 to about 0.01 inch. The maximum wall thickness of the braided reinforcing structure will be located at the cross points of the strands. The transverse and longitudinal dimensions of the catheter, the materials of construction, the number and spacing of the reinforcing strands will vary depending upon the end use of the catheter. The strands forming the braided reinforcing structure can be formed of a variety of materials include stainless steel (304) and high strength alloys such as MP35N, Elgiloy and L-605 which contain cobalt, chromium and nickel. The high strength alloys generally contain about 28 to about 65% cobalt, about 2 to about 40% nickel, about 5 to about 35% chromium and preferably also contain up to about 12% molybdenum, up to about 20% tungsten, up to about 20% iron and inconsequential amounts of other elements either as positive additions or impurities. The high strength alloy strands are preferably precipitation hardened for optimum properties. High strength plastic strands (e.g. Kevlar) or mixtures of plastic and metallic strands may also be used to form the braided reinforcing structure.

The adapter 16 on the proximal end of the catheter and the nose piece for the adapter may be formed of conventional polymeric materials such as polycarbonate.

The inner layer 20 of the shaft 11 is preferably formed of lubricous material or have a lubricious inner surface. The presently preferred lubricious material is a fluoropolymer. The outer layer 21 is preferably a polyamide elastomer, e.g. a polyether block amide such as PEBAX 55 alone or blended with nylon or PEBAX materials with other durometers.

It will be apparent from the foregoing that, while particular forms of the invention have been illustrated and described, various modifications can be made without departing from the spirit and scope of the invention. Moreover, those skilled in the art will recognize that features shown in one embodiment of the invention may be utilized in other embodiments of the invention.

What is claimed is:

1. An intraluminal catheter comprising an elongated shaft having proximal and distal ends, a port in the distal end, a wall defining an inner lumen extending within the elongated shaft which is in fluid communication with the port in the distal end, and a multistrand reinforcement extending to the port in the distal end, the multistrand reinforcement having strands secured together at a plurality of cross points.

2. The intraluminal catheter of claim 1 wherein the multistrand reinforcement is disposed within the wall defining the inner lumen.

3. The intraluminal catheter of claim 1 wherein the strands of the multistrand reinforcement are braided.

4. The intraluminal catheter of claim 1 wherein the strands of the multistrand reinforcement are wound.

5. The intraluminal catheter of claim 1 wherein the strands are secured together at the cross points by weldment.

6. The intraluminal catheter of claim 1 wherein the strands are secured together at the cross points by solder.

7. The intraluminal catheter of claim 1 wherein the strands are secured together at the cross points by adhesive.

8. The intraluminal catheter of claim 1 wherein the strands are secured together at the cross points by mechanical connections.

9. The intraluminal catheter of claim 1 wherein the strands are secured together at the cross points by brazement.

10. The intraluminal catheter of claim 1 wherein at least one of the strands is in the form of a wire.

11. The intraluminal catheter of claim 1 wherein at least one of the strands is in the form of a ribbon.

12. The intraluminal catheter of claim 1 wherein the strands are formed of a material selected from the group consisting of metals and plastics.

13. The intraluminal catheter of claim 1 wherein the strands are formed of a metal alloy selected from the group consisting of stainless steel, and chromium-cobalt-nickel alloys.

14. The intraluminal catheter of claim 1 wherein the strands are formed of a high strength polymeric material.

15. A method of forming a catheter comprising:
   a. providing an inner tubular member of polymeric material having proximal and distal ends, and a port in the distal end;
   b. braiding or winding a plurality of strands about the exterior of the inner tubular member of polymeric material into a reinforcing structure extending to the port of the distal end, the reinforcing structure having a plurality of cross point locations where the strands cross; and
   c. securing the strands at a plurality of cross point locations of the reinforcing structure.

16. The method of claim 15 wherein at least part of the reinforcing structure is held in a desired shape while the strands at a plurality of the cross point locations are secured together.

17. The method of claim 15 wherein an outer polymer layer is applied to the exterior of the reinforcing structure.

18. The method of claim 17 wherein the outer polymer layer is applied by heat shrinking.

19. The method of claim 15 wherein the strands are secured together at their cross point locations by welding.

20. The method of claim 15 wherein the strands are secured together at their cross point locations by soldering.

21. The method of claim 15 wherein the strands are secured together at their cross point locations by brazing.

22. The method of claim 15 wherein the strands are secured together at their cross point locations by a mechanical connection.

23. The method of claim 22 wherein the mechanical connection securing the strands together is effected by clips.

24. The method of claim 15 wherein the strands are secured together at cross point locations by applying an adhesive.

25. The method of claim 15 wherein at least half of the cross points or the multistrand reinforcement structure are secured together.

26. A method of forming a guiding catheter comprising:
   a. providing an inner tubular member of polymeric material;
   b. braiding or winding a plurality of strands about the exterior of the inner tubular member of polymeric material into a reinforcing structure having a plurality of cross point locations where the strands cross, with at least two of said strands being metallic and having a coating of solder on the exterior thereof; and
   c. heating the solder coated metallic strands at a plurality of cross point locations to melt the solder and cause the melted solder to flow about the strands at the cross point locations so as to secure the strands together into a reinforcing structure when the molten solder solidifies.

27. The method of claim 26 wherein an outer polymer layer is applied to the reinforcing structure.

28. The method of claim 26 wherein the outer polymer layer is applied by heat shrinking the outer polymer layer onto the exterior of the reinforcing structure.

29. The method of claim 26 wherein an outer polymeric layer is heat shrunk simultaneously when the strands are heated to melt the solder on the strands.

30. The method of claim 26 wherein at least part of the inner tubular member and the strands surrounding the inner tubular member are held in a desired shape when the strands are secured together at the cross point locations thereof.

31. The method of claim 30 wherein the inner tubular member and the strands surrounding the inner tubular member are held in a desired shape by placing a mandrel of the desired shape within the inner lumen of the inner tubular member.

32. In a guiding catheter comprising an elongated shaft having proximal and distal ends, a first port in the proximal end and a second port in the distal end, an inner lumen extending within the elongated shaft which is in fluid communication with the second port in the distal end and a multistrand reinforcing structure which has a plurality of cross point locations where the strands cross and which is disposed within the wall of the elongated shaft, the improvement comprising the multistrand reinforcing structure having strands at a plurality of cross point locations secured together to stiffen the reinforcing structure, and the multistrand reinforcing structure extends to the second port.

33. The guiding catheter of claim 32 wherein a distal portion of the elongated shaft has a desired shape to facilitate placement within a human body lumen.

* * * * *